wski et al.

(12) United States Patent
Komorowski et al.

(10) Patent No.: US 8,431,135 B2
(45) Date of Patent: Apr. 30, 2013

(54) POLYPEPTIDES AND METHODS FOR THE SPECIFIC DETECTION OF ANTIBODIES IN PATIENTS WITH A BORRELIA INFECTION

(75) Inventors: Lars Komorowski, Ratzeburg (DE); Christian Probst, Herrnburg (DE); Anthonina Janssen, Schiphorst (DE); Winfried Stöcker, Groβ Grönau (DE)

(73) Assignee: Euroimmun Medizinische Labordiagnostika AG, Lübeck (DE)

( * ) Notice: Subject to any disclaimer, the term of this patent is extended or adjusted under 35 U.S.C. 154(b) by 0 days.

(21) Appl. No.: 13/427,181

(22) Filed: Mar. 22, 2012

(65) Prior Publication Data

US 2012/0177680 A1 Jul. 12, 2012

Related U.S. Application Data

(62) Division of application No. 12/636,530, filed on Dec. 11, 2009, now Pat. No. 8,163,500.

(30) Foreign Application Priority Data

Dec. 12, 2008 (EP) .................................. 08021660

(51) Int. Cl.
*A61K 39/02* (2006.01)
(52) U.S. Cl.
USPC ...................................................... 424/190.1
(58) Field of Classification Search ........................ None
See application file for complete search history.

(56) References Cited

FOREIGN PATENT DOCUMENTS

| EP | 1741718 A2 | 1/2007 |
|---|---|---|
| EP | 1741718 A3 | 3/2007 |
| WO | 9514781 A2 | 6/1995 |
| WO | 9742221 A1 | 11/1997 |
| WO | 9749812 A2 | 12/1997 |

OTHER PUBLICATIONS

Abaza et al., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," *Journal of Protein Chemistry* 11(5):433-444, 1992.
Cruse et al., Illustrated Dictionary of Immunology, 2$^{nd}$ ed., CRC Press, 2003, pp. 46, 166, and 382.
Cutler et al., "Comparison of immunofluorescence and enzyme linked immunosorbent assays for diagnosing Lyme disease," *J. Clin. Pathol.* 42:869-871, 1989.
Earnhart et al., "Demonstration of OspC Type Diversity in Invasive Human Lyme Disease Isolates and Identification of Previously Uncharacterized Epitopes That Define the Specificity of the OspC Murine Antibody Response," *Infect. Immun.* 73(12):7869-7877, Dec. 2005.

Eicken et al., "Crystal Structure of Lyme Disease Variable Surface Antigen VlsE of *Borrelia burgdorferi*," *J. Biol. Chem.* 277(24):21691-21696, 2002.
Fister et al., "Comparative Evaluation of Three Products for the Detection of *Borrelia burgdorferi* Antibody in Human Serum," *J. Clin. Microbiol.* 27(12):2834-2837, Dec. 1989.
Fuchs et al., "Molecular analysis and expression of a *Borrelia burgdorferi* gene encoding a 22 kDa protein (pC) in *Escherichia coli*," *Mol. Microbiol.* 6(4):503-509, 1992.
Gilmore et al., "Conformational Nature of the *Borrelia burgdorferi* B31 Outer Surface Protein C Protective Epitope," *Infection and Immunity* 67(10):5463-5469, Oct. 1999.
Hagman et al., "Decorin-Binding Protein of *Borrelia burgdorferi* is Encoded within a Two-Gene Operon and is Protective in the Murine Model of *Lyme borreliosis*," *Infect. Immun.* 66(6):2674-2683, Jun. 1998.
Hansen et al., "Measurement of Antibodies to the *Borrelia burgdorferi* Flagellum Improves Serodiagnosis in Lyme Disease," *J. Clin. Microbiol.* 26(2):338-346, Feb. 1988.
Hauser et al., "Diagnostic Value of Proteins of Three *Borrelia* Species (*Borrelia burgdorferi* Sensu Lato) and Implications for Development and Use of Recombinant Antigens for Serodiagnosis of *Lyme borreliosis* in Europe," *Clin. Diagn. Lab. Immunol.* 5(4):456-462, Jul. 1998.
Hyde et al., "*Borrelia burgdorferi* Alters Its Gene Expression and Antigenic Profile in Response to CO2 Levels," *J. Bacteriol.* 189(2):437-445, Jan. 2007.
Kumaran et al., "Crystal structure of outer surface protein C (OspC) from the Lyme disease spirochete, *Borrelia burgdorferi*," *EMBO J.* 20(5):971-978, 2001.
Lawrenz et al., "Human Antibody Responses to VlsE Antigenic Variation Protein of *Borrelia burgdorferi*," *J. Clin. Microbiol.* 37(12):3997-4004, Dec. 1999.
Mathiesen et al., "The Dominant Epitope of *Borrelia garinii* Outer Surface Protein C Recognized by Sera from Patients with Neuroborreliosis has a Surface-Exposed Conserved Structural Motif," *Infect. Immun.* 66(9):4073-4079, Sep. 1998.
Mathiesen et al., "Peptide-Based OspC Enzyme-Linked Immunosorbent Assay for Serodiagnosis of *Lyme borreliosis*," *J. Clin. Microbiol.* 36(12):3474-3479, Dec. 1998.
McGuinness et al., "Class 1 outer membrane protein of *Nesseria meningitides*: epitope analysis of the antigenic diversity between strains, implications for subtype definition and molecular epidemiology," *Mol. Microbiol.* 7:505-514, Feb. 1993.
Moudallal et al., "Monoclonal antibodies as probes of the antigenic structure of tobacco mosaic virus," *EMBO Journal* 1(8):1005-1010, 1982.
Norris et al., "Low-Passage-Associated Proteins of *Borrelia burgdorferi* B31: Characterization and Molecular Cloning of OspD, a Surface-Exposed, Plasmid-Encoded Lipoprotein," *Infect. Immun.* 60(11):4662-4672, Nov. 1992.

(Continued)

*Primary Examiner* — Brian J Gangle
(74) *Attorney, Agent, or Firm* — SEED IP Law Group PLLC

(57) ABSTRACT

The present disclosure relates to proteins derived from OspC from bacteria of the genus *Borrelia*, in particular a protein which comprises a first OspC polypeptide, wherein the first OspC polypeptide is linked to a second OspC polypeptide via a disulphide bridge. The disclosure also relates to a method for the detection of antibodies against OspC and a method for the detection of a *Borrelia* infection, wherein a protein according to the disclosure is employed, and also to a diagnostic kit and a vaccine against *Borrelia*.

10 Claims, 2 Drawing Sheets

OTHER PUBLICATIONS

Novagen, Novagen His Tag GST Tag Purification and Detection Tools catalog, 2002.

Pollack et al., "Standardization of Medium for Culturing Lyme Disease Spirochetes," *J. Clin. Microbiol.* 31(5):1251-1255, May 1993.

Rauer et al., "Enzyme-Linked Immunosorbent Assay Using Recombinant OspC and the Internal 14-kDa Flagellin Fragment for Serodiagnosis of Early Lyme Disease," *J. Clin. Microbiol.* 36(4):857-861, Apr. 1998.

Rauer et al., "The Outer Surface Protein C (OspC) from *Borrelia burgdorferi* Can Appear as a Dimeric Molecule in Western Blot," *J. Spirochetal and Tick-borne Diseases* 3(2):105-108, Jun. 1996.

Ruzic-Sabljic et al., "Comparison of growth of *Borrelia afzelii, B. garinii*, and *B. burgdorferi* sensu stricto in MKP and BSK-II Medium," *Int. J. Med. Microbiol.* 294:407-412, 2004.

Seshu et al., "Dissolved Oxygen Levels Alter Gene Expression and Antigen Profiles in *Borrelia burgdorferi*," *Infect. Immun.* 72(3):1580-1586, Mar. 2004.

Wilske et al., "Immunological and Molecular Polymorphisms of OspC, an Immunodominant Major Outer Surface Protein of *Borrelia burgdorferi*," *Infect. Immun.* 61(5):2182-2191, May 1993.

Wilske et al., "Phenotypic Analysis of Outer Surface Protein C (OspC) of *Borrelia burgdorferi* Sensu Lato by Monoclonal Antibodies: Relationship to Genospecies and OspA Serotype," *J. Clin. Microbiol.* 33(1):103-109, Jan. 1995.

Wu et al., "Biogenesis of Lipoproteins in Bacteria," *Curr. Top. Microbiol. Immunol.* 125:127-157, 1986.

Yang et al., "Influence of Cultivation Media on Genetic Regulatory Patterns in *Borrelia burgdorferi*," *Infect. Immun.* 69(6):4159-4163, Jun. 2001.

```
CLUSTAL 2.0.10 multiple sequence alignment

VS461      CNNSGKG3DIASTNPDESAKGPNLTEISKKITDSNAVVLAVKEVEALLSSIDELA-KTIG  59
B31        CNNSGKDGNTSANSADESVKGPNLTEISKKITDSNAVLLAVKEVEALLSSIDEIAAKAIG  60
20047      CNNSG--GDTASTNPDESVKGPNLTEISKKITDSNAPVLAVKEVEALISSIDELA-KAIG  57
           *****   * : ::, .***:*********** *:***********:****:**  ***

VS461      KKIEAN-GLGNEADKNGSLLAGAYAISTLIKQKLDGLKGLEGLNKEIAEAKKCSEAFTKK  118
B31        KKIHQNNGLDTENNHNGSLLAGAYAISTLIKQKLDGLK-NEGLKEKIDAAKKCSETFTNK  119
20047      QRIQQN-GLVADAGHNSALLAGAHEISILITQKLDGLKGLEGLIKAEIAEAKKYSEAFTKK  116
           :: : * **  * ::*** ***:::**:*******  * ** *: * *:**:**:::*

VS461      LQDSNADLGKHN--ATDADSKEAILKTNGTKTKGAKELBELFKSVESLSKAAKEALSNSV  176
B31        LKEKHTDLGKEG--VTDADAKEAILKTNGTKTKGAEELGKLFESVEVLSKAAKEMLANSV  177
20047      LKDNHAQLGIQMGASLDDEAKKAILKTNVDKTTKGAEELEKLFKSVESLSKAAQEALTNSV  176
           *: : ** :   .  *::*:*****    **** **:*:***:*** :**:*:* *:**

VS461      KELTSPVVAESPKKP   191
B31        KELTSPVVAESPKKP   192
20047      KELTNPVVAETPKKP   191
           ****.****** ***
```

| SeqA | Name  | Len(aa) | SeqB | Name  | Len(aa) | Score |
|------|-------|---------|------|-------|---------|-------|
| 1    | VS461 | 195     | 2    | B31   | 195     | 76    |
| 1    | VS461 | 195     | 3    | 20047 | 195     | 76    |
| 2    | B31   | 195     | 3    | 20047 | 195     | 70    |

FIG. 1

POLYPEPTIDES AND METHODS FOR THE SPECIFIC DETECTION OF ANTIBODIES IN PATIENTS WITH A BORRELIA INFECTION

CROSS-REFERENCES TO RELATED APPLICATIONS

This application is a divisional of U.S. patent application Ser. No. 12/636,530, filed Dec. 11, 2009, now issued as U.S. Pat. No. 8,163,500 which application claims the benefit under 35 U.S.C. §119 of European Patent Application No. 08021660.9, filed Dec. 12, 2008, where these applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 310159_404D1 SEQUENCE_LISTING_.txt. The text file is 29 KB, was created on Mar. 19, 2012, and is being submitted electronically via EFS-Web.

BACKGROUND

1. Technical Field

The present disclosure relates to polypeptides derived from OspC ("outer surface protein C") from bacteria of the genus *Borrelia*, in particular a protein which comprises a first OspC polypeptide, wherein the first OspC polypeptide is linked to a second OspC polypeptide via a disulphide bridge. The disclosure also relates to a method for the detection of antibodies against OspC and a method for the detection of a *Borrelia* infection, wherein a protein according to the disclosure is employed, and also to a diagnostic kit and a vaccine against *Borrelia*.

2. Description of the Related Art

Bacteria of the genus *Borrelia* are described as pathogens of several human diseases, in particular as pathogens of Lyme borreliosis and of relapsing fever. An infection nowadays is usually detected via determination of specific antibodies against the bacteria in human or animal body fluids. In this context, the presence of specific antibodies against antigens which occur only in *Borrelia* indicates an infection with *Borrelia*. Early phases of infection, in particular fresh infections up to four weeks after initial contact, are characterized by the presence of antibodies of the IgM class, in particular against the antigens OspC, p41 (flagellin) and P39 (BmpA), while late phases, in particular infections which have run their course, have been cured or are chronically manifest, are accompanied by the presence of antibodies of the IgG class, in particular against the antigens VlsE, p83/P100, p58, OspA, p41 (flagellin), P39, P18 and others (Wilske and Fingerle, 2005).

An early diagnosis of the disease is particularly important because therapy with antibiotics is more successful and easier in the early stages than in late stages, thus, e.g. in the early phase, an oral therapy with antibiotics is still possible.

Antibodies against OspC of the IgM class are generally the most important marker for an early phase of the disease. Native OspC is a membrane protein of the lipoprotein family 6 acylated with a fatty acid, which is anchored in the outer cell membrane (Norris et al., 1992; Hagman et al., 1998). During expression, in parallel with the cleavage of the signal sequence by signal peptidase II, the acyl residue is attached to the only conserved cysteine occurring in the OspC amino acid sequence (Wu and Tokunaga, 1986). It serves for anchoring in the lipid-containing cell membrane.

A conserved C-terminal peptide of ten amino acid residues, the terminal carboxyl group of which must be freely accessible, is generally regarded as the most important epitope within OspC for reactions with human antibodies of the IgM class (Mathiesen et al., 1998a; Mathiesen et al., 1998b), as is also described in the PCT patent specification WO 9742221. Epitopes in the poorly conserved central region of OspC are also described (Earnhart et al., 2005).

For detection of the antibodies, antigens purified from *Borrelia* are regularly used in immunobiochemical tests, such as ELISA, line blot or western blot. In the methods, individual or several antigens are conventionally bound to a solid phase and brought into contact with the body fluid to be analysed, and the bound antibodies are detected by a reporter molecule. Such kits are marketed e.g. by EUROIMMUN AG as EUROLINE-WB and Anti-*Borrelia*-plus-VIsE-ELISA. Similar methods are described in the literature (Hansen et al., 1988; Cutler and Wright, 1989; Fister et al., 1989).

Methods which are based on non-recombinant preparations can be reproduced only with a high outlay and are therefore cost-intensive, because essentially complex culture media which contain natural constituents which are not chemically defined, such as protein-containing serum fractions from *Mammalia* and complex protein mixture, e.g. proteolytically treated muscle extracts, yeast extracts or gelatine, are used for in vitro culturing of *Borrelia*. A commercial kit on this basis is obtainable e.g. from Sigma Aldrich (Complete BSK-H). Similar compositions are described in the literature with the designations MKP and BSK II (Ruzic-Sabljic and Strle, 2004).

Unfortunately, the constituents of these media which are not chemically defined are subject to marked variations in their compositions from batch to batch, are at risk of contamination with viruses or Mycoplasma and are cost-intensive to produce. Accordingly, *Borrelia* cultured in vitro conventionally show marked variations in their growth rates and their gene expression patterns, depending on the particular culture media used or depending on individual components of the particular culture media used. Genes which are expressed in vivo, depending on the particular host organism, are particularly affected by this (Pollack et al., 1993; Yang et al., 2001). This applies in particular to OspC. The culturing temperature and the oxygen and carbon dioxide concentration furthermore also have a decisive influence on the nature and amount of the proteins expressed (Seshu et al., 2004; Hyde et al., 2007). As a result, in particular the results from different laboratories which culture *Borrelia* can be poorly compared with one another.

Methods which are based on individual antigens purified from *Borrelia* cultured in vitro are furthermore susceptible to non-specific reactions caused by the presence of further impurities which have not been adequately depleted. In particular, in methods which only generate one signal, such as, for example, ELISA or line blot, falsely positive results are thus regularly obtained. In contrast, western blots, which bypass this problem by local resolution of the signals, have the disadvantage that they generate a considerable additional effort due to the required electrophoresis and the transfer to a membrane.

In further methods, antigens are used which are prepared by recombinant techniques, e.g. by heterologous expression of antigens or antigen fragments in *E. coli*, as described e.g. in the European patent specification EP 0506868. Commercially obtainable variants are e.g. EUROLINE-WB and Anti-

*Borrelia*-plus-VIsE-ELISA (IgG) and the recomline *Borrelia* IgM (Mikrogen). Similar methods are described in the literature (Hauser et al., 1998; Lawrenz et al., 1999; Wilske and Fingerle, 2005). In general, recombinant antigens have the advantage that they can be purified in a more defined manner and with less effort than native antigens, e.g. by fusion with purification polypeptides, e.g. the polyhistidine-tag (=His-tag).

Heterologous expression of OspC including its intrinsic signal sequence in *E. coli* and subsequent acylation is possible, but leads to a low expression efficiency (Fuchs et al., 1992). For this reason, in general deletion constructs of OspC with increased expression efficiency in which at least the signal sequence is missing are employed. In this context, in the prior art, at least the first 19 amino acids of OspC, including the cysteine which occurs in the OspC amino acid sequence, are deleted (Fuchs et al., 1992; Wilske et al., 1993; Wilske et al., 1995; Eicken et al., 2001; Kumaran et al., 2001), and this is in some cases supplemented by N-terminal fusion with heterologous polypeptides, e.g. the His-tag.

Such N-terminally shortened variants have also been used for clarification of the spatial structure of OspC (Kumaran et al., 2001; Eicken et al., 2001). For this, the first 31 (Eicken et al., 2001) or 37 (Kumaran et al., 2001) amino acid residues of OspC were deleted in the recombinant OspC variants in order to achieve in particular a suitable amount and purity of the OspC. The two exemplary spatial structures indicate that recombinant OspC tends to dimerize. This dimerization takes place on the basis of ionic interactions and hydrogen bridge bonds, but not by a covalent linking.

There are also attempts to prepare acylated variants of OspC recombinantly by upstream insertion of a heterologous signal sequence, as described e.g. in the European patent specification EP 1741718. By attaching the fatty acid, such OspC variants are intended to have a higher in vivo immunogenicity than the N-terminally deleted or modified OspC variants described until then.

The recombinant variants of OspC used hitherto for diagnostics in general have the disadvantage that they differ from the native OspC purified from *Borrelia* cultured in vitro, because they are not or are differently modified post-translationally, and the presence of conformational epitopes or the accessibility of epitopes in general is not comparable or not guaranteed. The manifestation of these disadvantages is the lower specific reactivity of recombinant OspC variants used to date compared with non-recombinant preparations, which is regularly described in the literature. It is reflected in high rates of false positive results in such diagnostic methods.

The development of recombinant OspC variants which, with an easier and more defined preparation compared with the native antigens, can be employed in diagnostic methods and at the same time do not lead to the disadvantages described for the recombinant OspC variants to date is therefore necessary in order to facilitate the preparation of such in vitro diagnostic agents or the implementation of such diagnostic methods and to standardize the results of different laboratories.

BRIEF SUMMARY

In one aspect, the present disclosure provides a protein that comprises a first OspC polypeptide and a second OspC polypeptide, wherein the first OspC polypeptide is linked to the second OspC polypeptide via a disulphide bridge.

In another aspect, the present disclosure provides a method for detecting antibodies in a biological sample against the above-described protein, comprising: contacting the biological sample with the protein, and detecting binding of antibodies to the protein.

In another aspect, the present disclosure provides a method for diagnosing a *Borrelia* infection, comprising contacting a biological sample of a patient with the above-described protein, and determining the presence or absence of binding of antibodies that may be in the sample to the protein, wherein the presence of the binding of antibodies to the protein indicates a *Borrelia* infection.

In another aspect, the present disclosure provides a kit for diagnosing a *Borrelia* infection, comprising the above-described protein.

In another aspect, the present disclosure provides a method for vaccinating against a *Borrelia* infection, comprising administering the above-described protein to a patient.

In another aspect, the present disclosure provides a vaccine against a *Borrelia* infection, comprising the above-described protein.

BRIEF DESCRIPTION OF THE DRAWINGS

FIG. 1 shows an alignment of mature OspC from *B. afzelii* VS461=OspC$_{VS461}$ (SEQ ID NO:3), from *B. garinii* 20047=OspC$_{20047}$ (SEQ ID NO:6) and from *B. burgdorferi* B31=OspC$_{B31}$ (SEQ ID NO:9), determined with CLUSTAL 2.0.10 with standard settings. The table shows the degree of amino acid identity.

DETAILED DESCRIPTION

Figure 2:
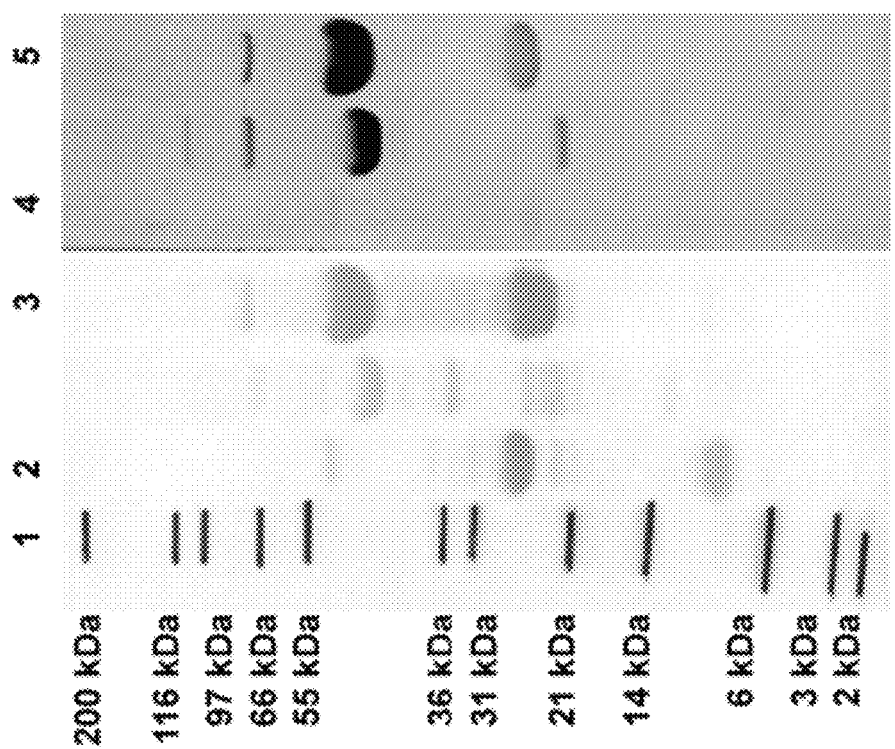
FIG. 2 shows by way of example a western blot with the non-reduced variants His-m-OspC$_{VS461}$ and His-m-Cys-OspC$_{VS461}$ after staining with Ponceau S (track 1-3) and after incubation with a serum of a patient with a borreliosis in the early stage (1:200 dilution) and detection of the bound IgM antibodies (track 4 & 5). Track 1: size marker Mark12 (Invitrogen), track 2 & 4: 15 µg of His-m-OspC$_{VS461}$, track 3 & 5: 25 µg of His-m-Cys-OspC$_{VS461}$.

It has now been found, surprisingly, that the problems described can be solved by the disclosure, in particular the subject matter of the claims.

The disclosure provides a protein comprising a first OspC polypeptide, wherein the first OspC polypeptide is covalently linked to a second OspC polypeptide. It has proved advantageous in the context of the disclosure if the first OspC polypeptide is linked to a second OspC polypeptide via a disulphide bridge.

An OspC polypeptide in the context of the disclosure, in particular the first and/or second OspC polypeptide, can have an amino acid identity of at least 70% with SEQ ID NO:3, SEQ ID NO:6 or SEQ ID NO:9 and is recognized (in this homologous region) specifically by antibodies against OspC from *Borrelia*. Preferably, the amino acid identity is at least 80%, at least 90%, at least 95% or at least 99% to one or more of the sequences according to SEQ ID NO:3, SEQ ID NO:6 or SEQ ID NO:9. These sequences correspond to the native OspC sequences from the three type strains of the *Borrelia* genospecies *Borrelia afzelii* (VS461), *Borrelia garinii* (20047) and *Borrelia burgdorferi* (B31). The amino acid identity between these strains is 70% and 76% (see FIG. 1). The amino acid identity is preferably determined with the program CLUSTAL 2.0.10 with standard settings. In the context of the disclosure, in particular, an OspC sequence from another *Borrelia* strain, e.g. PKo, or a variant thereof can be employed, the specific binding by antibodies against OspC from *Borrelia* being decisive.

In the context of the disclosure, a specific recognition by antibodies against OspC from *Borrelia* means that under conditions suitable for this, which are known to the person skilled in the art and described, for example, in the examples, antibodies against OspC from *Borrelia* bind to the polypeptide or protein, but not to another unrelated protein. Serum from patients with a confirmed early phase of a *Borrelia* infection can be employed, for example, as antibodies against OspC from *Borrelia*, as can antibodies which have been produced e.g. by immunization of mice or rabbits with native purified OspC (e.g. EUROIMMUN), in particular polyclonal antibodies.

*Borrelia* includes all bacteria of the genus *Borrelia*, and *B. burgdorferi, B. garinii* and *B. afzelii* are mentioned by way of example.

An OspC polypeptide in the context of the disclosure, in particular the first and/or second OspC polypeptide, may comprise at least one epitope which is specifically recognized by antibodies against OspC from *Borrelia*, the epitope comprising at least a partial sequence of 10 contiguous amino acids from SEQ ID NO:3, SEQ ID NO:6 or SEQ ID NO:9, in particular the 10 C-terminal amino acids of these sequences. Preferably, the partial sequence comprises the epitope described as immunodominant in Mathiesen et al., 1998a; Mathiesen et al., 1998b. In particular, the OspC polypeptide(s) comprise(s) one of the amino acid sequences according to SEQ ID NO:2, SEQ ID NO:5 or SEQ ID NO:8 in the C-terminal location. It is preferable for the OspC polypeptide(s) to end at the C-terminus with the sequence of the native OspC, that is to say no further amino acids which could impede the recognition of the C-terminal epitope are contained here.

Alternatively or in addition, one or more further epitopes, e.g. as described by Earnhart et al., 2005, can be present in the OspC polypeptide.

Preferably, the epitope is or the epitopes are embedded in further sequences from OspC corresponding to a wild type sequence from OspC from *Borrelia*. Preferably, the partial sequence of contiguous amino acids from SEQ ID NO:3, SEQ ID NO:6 or SEQ ID NO:9 has a length of at least 15, at least 20, at least 25, at least 30, at least 50, at least 100, at least 150 or at least 190 amino acids. Preferably, these are the C-terminal amino acids from SEQ ID NO:3, SEQ ID NO:6 or SEQ ID NO:9, from homologues from other *Borrelia* strains or homologues with a sequence identity of at least 70%, at least 80%, at least 90%, at least 95% or at least 99% with SEQ ID NO:3, SEQ ID NO:6 or SEQ ID NO:9.

The OspC polypeptides according to the disclosure contain no signal sequences for an acylation. Polypeptides expressed in the prior art (EP 1741718) which, like the wild type polypeptide, were to be acylated on the furthest N-terminally located cysteine, were expressed with a heterologous signal sequence. In contrast, the polypeptide according to the disclosure contains neither a homologous signal sequence nor a heterologous signal sequence. Signal sequences which lead to an acylation conventionally comprise a Braun's signal sequence which is recognized by signal peptidase II. Such signal sequences can comprise e.g. the sequence L-I-A-C (as OspA or OspB) or L-X-Y-C (wherein X and Y are small neutral amino acids) (Fuchs et al., 1992). Preferably, the polypeptide according to the disclosure also was not expressed with an acylation sequence, this then being split off. The OspC polypeptide according to the disclosure is therefore also not acylated. In one embodiment of the disclosure, the cysteine on which the acylation would take place in the wild type OspC is the cysteine on which the disulphide bridge to a further OspC polypeptide is formed.

Alternatively or in addition, a disulphide bridge can also be formed on another cysteine. Preferably, the disulphide bridge is formed by bonding of a cysteine which is not more than about 100, preferably not more than about 50 or not more than about 30 amino acid positions from the N-terminus of the OspC polypeptide. In particular, the disulphide bridge can be formed on a cysteine which forms the N-terminus of the polypeptide or is 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids away from the N-terminus.

In order to facilitate the purification of the protein according to the disclosure, in one embodiment, on the N-terminus, in particular N-terminally from the cysteine on which the disulphide bridge is formed, the OspC polypeptide/the OspC polypeptides contain/contains a His-tag, which can have e.g. the sequence corresponding to the first 12 amino acids of SEQ ID NO:1. Instead of 8, e.g., 6 or 10 histidines can also be employed. Other amino acid sequences known in the prior art which facilitate purification or detection of the protein, e.g. a Flag-tag, can also be incorporated here. Such sequences should not impede the recognition by antibodies against OspC from *Borrelia*. Under this prerequisite, bonding or incorporation of a reporter molecule is also possible at another location in the molecule. The reporter molecule can be chosen, e.g., from a group comprising His-tag, Flag-tag, a fluorescence label, biotin and streptavidin.

In one embodiment, the first OspC polypeptide N-terminally comprises a His-tag, which is adjacent to a cysteine which is bonded to the second OspC polypeptide in the protein according to the disclosure via a disulphide bridge, and following this in the polypeptide chain of the first OspC polypeptide, the further sequence of an OspC polypeptide from a *Borrelia* strain, e.g. *B. burgdorferi, B. afzelii* or *B. garinii*, this sequence forming the C-terminus of the polypeptide. In particular, the OspC polypeptide can consist of these sequences. The second (and optionally further) OspC polypeptide preferably comprises the same sequence constituents (His-tag-Cys-OspC sequence) or consists of these.

In a preferred embodiment, the first and/or the second OspC polypeptide contains a sequence according to SEQ ID NO:2, SEQ ID NO:5 or SEQ ID NO:8.

In the context of the present disclosure, "a" in general is not used as a numerical word, but an indeterminate number can be described by this. Unless described otherwise, it can thus also represent two or more. In particular, in the context of the disclosure an OspC polypeptide is understood as meaning the first and/or the second OspC polypeptide of a protein according to the disclosure. This does not exclude the presence of further OspC polypeptides, which preferably have the same structure as the first OspC polypeptides.

Preferably, the proteins according to the disclosure are dimers of two OspC polypeptides. Multimerization with further OspC polypeptides or other molecules (e.g. via additional disulphide bridges) is also in principle possible, as long as this does not impede or restrict the recognition by antibodies against OspC from *Borrelia*. It has been demonstrated in the context of the disclosure that by means of the disulphide bridge, a homodimer of two identical OspC polypeptides or a heterodimer of different OspC polypeptides can be formed. With a protein according to the disclosure, it is therefore possible e.g. to conduct the detection of antibodies against several *Borrelia* strains, or to prepare a vaccine against several *Borrelia* strains.

With respect to the present disclosure, protein is in general used for multimers of OspC polypeptides and polypeptide for individual OspC polypeptide chains, but both terms, as can be seen by the person skilled in the art from the context in each case, can also relate to proteins, polypeptides or peptides according to general scientific usage, no differentiation being made between different sizes.

In the context of the disclosure, it has been demonstrated that the disulphide bridge bond directly between the OspC polypeptides significantly improves the recognition by antibodies against OspC from *Borrelia*. Associated with this, the recognition of the protein by antibodies against OspC from *Borrelia* is reduced by bringing it into contact with at least one reagent which destroys the disulphide bridge. In particular, such a reagent is chosen from a group comprising thiol-containing reagents or a combination of a thiol-containing reagent and an alkyl halide. Such reagents include e.g. reducing agents, such as dithiothreitol or mercaptoethanol, optionally in combination with an alkylating agent, such as iodoacetamide. In particular, a reducing agent can first be employed, and then an alkyl halide.

A protein according to the disclosure can be produced e.g. in bacterial cells (e.g. *E. coli*, e.g. *E. coli* RosettaBlue(DE3) pLacl (Stratagene)), insect cells (e.g. SF6 cells), yeast cells (e.g. *S. cerevisiae*) or cells of vertebrates (e.g. CHO cells). The disclosure includes a method for the production of the protein according to the disclosure wherein this is recombinantly expressed and purified. Purification is possible e.g. via affinity chromatography, it being possible to use, for example, antibodies against OspC from *Borrelia* or—if e.g. a His-tag is used—a nickel affinity chromatography. Preferably, non-reducing conditions are used for the expression and/or purification. Preferably, a pH of 7-9, a pH of 7.5-8.5, in particular pH 8 is used during the purification. In an affinity chromatography e.g. the mixture to be purified can be applied and washed with TNI110 buffer, and the protein can be eluted with TNI150 buffer. Other production and purification methods which do not impede the formation of the disulphide bridge are known in the prior art.

In one aspect, the present disclosure relates to a method for the detection of antibodies against a protein according to the disclosure, in which a biological sample is brought into contact with the protein according to the disclosure, and binding of antibodies, which may possibly be present in the sample, to the protein is detected.

In particular, a method for the diagnosis of a *Borrelia* infection is disclosed, in which a biological sample from a patient is brought into contact with a protein according to the disclosure, and binding of antibodies which may possibly be present in the sample to the protein is detected, wherein detection of the binding of antibodies indicates a *Borrelia* infection.

The disclosure also provides the use of a protein according to the disclosure for the detection of antibodies against OspC of *Borrelia* and for the diagnosis of a *Borrelia* infection. The antibodies detected are preferably antibodies of the IgM type, by which means a *Borrelia* infection in an early phase is detected.

The binding of the antibodies can be detected e.g. with an immunofluorescence test, ELISA, luminescence test, western blot, line blot or dot blot. The biological sample employed can be e.g. a body fluid of a patient, in particular blood, serum, plasma, saliva, urine or cerebrospinal fluid. Preferably, the patient is a human or animal patient who is to be tested, for example, for an infection with *Borrelia*.

The disclosure also provides a kit for the diagnosis of *Borrelia* infections comprising a protein according to the disclosure. Such a kit can furthermore comprise antibodies against OspC from *Borrelia* and/or buffers and/or reagents suitable for the detection, such as e.g. an antibody which recognizes human IgM, optionally marked with a reagent suitable for the detection (e.g. a fluorescent dye, such as FITC or PE, an enzyme, such as alkaline phosphatase or horseradish peroxidase, or biotin). It can be e.g. a kit for an immunofluorescence test, ELISA, luminescence test, western blot, line blot or dot blot.

The disclosure also provides the use of a protein according to the disclosure for the preparation of a vaccine against a *Borrelia* infection, and a vaccine against a *Borrelia* infection comprising a protein according to the disclosure. Such a vaccine may comprise suitable auxiliary substances, buffers and/or adjuvants. It can be a combination vaccine which, for example, can be directed against two, three or more *Borrelia* strains. This can be achieved by the use of heteromeric OspC proteins, but also e.g. by mixing various homodimers. Such a vaccine can be formulated e.g. for subcutaneous, intramuscular, intravenous or oral administration. Multiple administration, e.g. twice, three times or four times (for example on day 1, 14, 28, 42), may be appropriate in order to improve the formation of antibodies.

The present disclosure for the first time makes it possible to determine OspC-specific antibodies with the aid of recombinant OspC variants which give results which are diagnostically equivalent to the use of non-recombinant OspC variants. At the same time, the use of the novel recombinant OspC variants with disulphide bridges makes a considerable reduction in the effort for the production of the antigens possible, compared with the native OspC variants which were hitherto regarded as diagnostically the most competent.

It has been found that the OspC variants according to SEQ ID NO:1, SEQ ID NO:2 (derived from mature OspC according to SEQ ID NO:3 from *B. afzelii* VS461=OspC$_{VS461}$, Genbank Accession No. D49379), SEQ ID NO:4, SEQ ID NO:5 (derived from OspC according to SEQ ID NO:6 from *B. garinii* 20047=OspC$_{20047}$, Genbank Accession No. L42900), SEQ ID NO:7 and SEQ ID NO:8 (derived from OspC according to SEQ ID NO:9 from *B. burgdorferi* B31=OspC$_{B31}$, Genbank Accession No. U01894) can be expressed in large amounts in *E. coli* and can be prepared with a high purity. No difference was found in this context in the effort for the genetic engineering work, expression rate, effort for the preparation or purity between the variants according to SEQ ID NO:1 and SEQ ID NO:2 (derived from OspC$_{VS461}$), SEQ ID NO:4 and SEQ ID NO:5 (derived from OspC$_{20047}$) and SEQ ID NO:7 and SEQ ID NO:8 (derived from OspC$_{B31}$), which in each case differ by only one cysteine.

It has moreover been demonstrated by way of example that the diagnostic accuracy of a method for the determination of antibodies of the IgM class using the variant according to SEQ ID NO:2 derived from OspC$_{VS461}$ surprisingly is equivalent to an established method using non-recombinant OspC of the strain VS461. It has furthermore been demonstrated that the diagnostic accuracy of these two methods is greater than in methods which use the variant according to SEQ ID NO:1 derived from OspC$_{VS461}$ or recombinant OspC variants deleted in accordance with the scientific literature.

It has furthermore been demonstrated by way of example that the variant according to SEQ ID NO:2 derived from OspC$_{VS461}$ is present in a form dimerized via a disulphide bridge after biochemical purification, and that it surprisingly has a higher specific reactivity than its monomer, its monomer acetylated on the cysteine and the analogous monomer according to SEQ ID NO:1.

It has furthermore been demonstrated by way of example that by mixing the variants according to SEQ ID NO:2 (derived from OspC$_{VS461}$ and SEQ ID NO:5 (derived from OspC$_{20047}$), followed by reduction thereof and subsequent oxidation, heterodimers with disulphide bridges can be prepared, the usability of which is in principle equivalent to the homodimers with disulphide bridges, but which have the advantage of being able to detect several different species-specific antibodies, i.e. antibodies directed exclusively against OspC from *B. afzelii* strains or exclusively against OspC from *B. garinii* strains. Means and methods for separating heterodimers from homodimers, e.g. by isoelectric focussing, are accessible to the person skilled in the art. Such a separation is however not necessary, since mixtures of homodimers and heterodimers can also be used.

It has furthermore been demonstrated by way of example that mice surprisingly have a higher titre of antibodies against *Borrelia* after immunization with the OspC variant according to SEQ ID NO:2 (derived from OspC$_{VS461}$) dimerized via disulphide bridges than after immunization with the same amount of the monomeric OspC variant according to SEQ ID NO:1. A higher effectiveness of vaccines based on the polypeptides according to the disclosure can be concluded from this. The results can be applied to the other variants, to other animals and to humans.

The following examples present the subject matter of the disclosure by way of example, but are not intended to limit the disclosure. Modifications are obvious to the person skilled in the art. All the publications cited are included explicitly by the reference.

EXAMPLES

Example 1

Cloning of Vectors for Expression of OspC in *E. coli*

OspC is coded on plasmid B in *Borrelia* (nomenclature on the basis of the complete *B. burgdorferi* genome, reading frame BB_B19). Total DNA from *B. afzelii* strain VS461, *B. garinii* strain 20047 and *B. burgdorferi* strain B31 is used as the template for PCR amplification of gene regions according to SEQ ID NOS:10 to 15 coding for six OspC variants. The primer combinations according to SEQ ID NO:16 and SEQ ID NO:17 (His-m-OspC$_{VS461}$), SEQ ID NO:18 and SEQ ID NO:17 (His-Cys-m-OspC$_{VS461}$), SEQ ID NO:19 and SEQ ID NO:20 (His-m-OspC$_{20047}$), SEQ ID NO:21 and SEQ ID NO:20 (His-Cys-m-OspC$_{20047}$), SEQ ID NO:22 and SEQ ID NO:17 (His-m-OspC$_{B31}$) and SEQ ID NO:23 and SEQ ID NO:17 (His-Cys-m-OspC$_{31}$) are employed for amplification of the individual variants. By the PCR, the necessary restriction cleavage sites are integrated into the amplificates at the 5' and 3' end of the coding strand, respectively.

The PCR is carried out on a 50 µl scale using the "High Fidelity PCR Enzyme Mix" (Fermentas) according to the manufacturer's instructions. 30 reaction cycles composed of steps 1 to 3 are carried out:

| | | |
|---|---|---|
| Step 1 | 30 seconds | 94° C. |
| Step 2 | 45 seconds | 56° C. |
| Step 3 | 30 seconds | 72° C. |

The PCR fragments are then purified using the NucleoSpin® Extract II purification system (MACHEREY-NAGEL GmbH & Co. KG) in accordance with the manufacturer's instructions and taken up in each case in 50 µl of 5 mM Tris-HCl pH 8.5. The fragments are then cleaved at the ends by restriction endonucleases. The restriction endonucleases are obtained from Fermentas and employed in accordance with the manufacturer's instructions.

The amplificates are treated with restriction endonucleases as follows:

His-m-OspC$_{VS461}$: NcoI and XhoI,
His-Cys-m-OspC$_{VS461}$: Esp3I and XhoI,
His-m-OspC$_{20047}$: NcoI and XhoI,
His-Cys-m-OspC$_{20047}$: Esp3I and XhoI,
His-m-OspC$_{B31}$: NcoI and XhoI,
His-Cys-m-OspC$_{B31}$: PagI and XhoI.

The PCR fragments are then purified using the NucleoSpin® Extract II purification system in accordance with the manufacturer's instructions and taken up in 50 µl of 5 mM Tris-HCl pH 8.5, respectively.

The enzymatically cleaved and purified PCR fragments are then integrated into NcoI/XhoI-cleaved plasmid according to SEQ ID NO:24 by ligation. The Rapid DNA Ligation Kit from Fermentas is employed for the ligation in accordance with the manufacturer's instructions. The ligation batch is transformed into *E. coli* RosettaBlue(DE3)pLacI (Stratagene).

Positive clones are selected on the basis of kanamycin/chloramphenicol [50/34 µg/ml] resistance. The plasmids contained in these clones are isolated from them and checked by restriction analysis and DNA sequencing. Correct plasmids are chosen for carrying out the expression, inoculated into 20 ml of LB medium containing antibiotics and incubated at 37° C. until an OD600 (d=1 cm) of 0.6 is reached. The protein expression is induced by addition of IPTG (final concentration: 1 mM) and incubation is then carried out for a further 3 hours at 37° C. After this time, the cells are sedimented by centrifugation at 2,200×g for 10 minutes, resuspended in 20 ml of PBS, centrifuged again and finally resuspended in 1 ml of PBS.

The cells are broken down by addition of one third volume of 4×NuPAGE-LDS sample buffer (Invitrogen), containing 141 mM Tris-HCl pH 8.5, 2%) (w/v) lithium dodecyl sulphate, 10% (w/v) glycerol, 0.51 mM EDTA, 0.22 mM SERVA Blue G250, followed by incubation for 10 minutes at 70° C. Chromosomal DNA is then fragmented by ultrasound treatment (Branson Sonifier, level 7, MicroTip).

After separation by SDS-PAGE, the cell lysate is transferred to a nitrocellulose membrane. Non-saturated positions of the membrane are then blocked by incubation with "universal buffer" (EUROIMMUN) with 3% (w/v) milk powder for 15 minutes. Incubation is then carried out for 1 hour with a monoclonal antibody from the mouse (Merck Biosciences GmbH) directed against the His-tag and diluted 1:2,000 in "universal buffer" with 3% (w/v) milk powder. Washing is then carried out with "universal buffer" three times for 5 minutes each time. In a second incubation step, the antibodies bound to the proteins in the positive case react with a conjugate solution which is diluted 1:2,000 in "universal buffer" and contains as the conjugate an anti-mouse IgG antibody labelled with alkaline phosphatase (Sigma). Washing is then carried out as after the anti-His-tag incubation. In a third incubation step, the bound antibodies are then detected with an NBT/BCIP "substrate solution" (4-nitroblue tetrazolium chloride/chlorobromoindolyl phosphate, EUROIMMUN).

Results:

In the western blot after reducing SDS-PAGE, the expression of the recombinant constructs can be detected by the presence of His-tag-reactive proteins, the sizes of which are in good agreement with the masses of 23-25 kDa predicted on the basis of the amino acid sequences. Cells which contain the unchanged plasmid vector contain no corresponding protein.

Example 2

Purification of Recombinant OspC Variants by Affinity Chromatography

The affinity column is a NiNTA spin column (Qiagen) handled in accordance with the manufacturer's recommendations.

The cells harvested according to Example 1 are centrifuged again as described, resuspended in 1 ml of "TNI10 buffer" (5 mM Tris-HCl pH 8.0; 300 mM NaCl; 10 mM imidazole) and broken down by three ultrasound treatments of one minute (Branson Sonifier, level 7, MicroTip). 0.5 ml of the supernatant is applied to a NiNTA spin column equilibrated with "TNI10 buffer".

Non- or weakly bound proteins are removed from the column by washing several times with 0.5 ml of "TNI10 buffer". Elution is carried out with 0.2 ml of "TNI150 buffer" (5 mM Tris-HCl pH 8.0; 300 mM NaCl; 150 mM imidazole). The elution fraction is analysed by western blot as in Example 1.

Results:

The eluates essentially contain proteins which, after staining of the western blot membrane with Ponceau S staining solution, in each case correspond to bands corresponding to a size of about 23-25 kDa. After western blot and detection of the His-tag, a bond corresponding to the same size can be seen. This result indicates that after the chromatography, the protein expressed is present in a form essentially free from *E. coli* constituents.

Example 3

Line Blots for Determination of Anti-OspC Antibodies with the Aid of the Recombinant OspC Variants Nitrocellulose membranes are coated in lines with a purified recombinant OspC according to Example 2 diluted in 10% (w/v) glycerol (concentration: 20-100 µg/ml). The membranes are then dried overnight, blocked for 1 hour with "universal buffer" (EUROIMMUN), fixed on a solid phase, cut into strips about 2 mm wide with a scalpel at a 90° angle to the OspC lines, and then stored at 4° C. in aluminium bags with desiccant bags until used. The strips are incubated as described in the working instructions for EUROLINE-WB strips (EUROIMMUN), which are incubated as a comparison. Incubation of recomLine *Borrelia* strips (Microgen) in accordance with the manufacturer's instructions serves as a further comparison.

For determination of the sensitivity and specificity, 25 serum samples from patients with confirmed early phase of a *Borrelia* infection and 50 serum samples from pregnant women (which frequently contain non-specific antibodies) without signs of a *Borrelia* infection and 25 serum sample pairs from healthy persons taken at an interval of 14 days are analysed with respect to the presence of OspC-specific antibodies of immunoglobulin class M (IgM). Positive reactions in the healthy persons are checked by analysis of the IgG seroconversion (comparison of day 0/day 14) with several test systems for detection of antibodies of the IgG class against *Borrelia*, e.g. EUROLINE-WB IgG and anti-*Borrelia* ELISA IgG (EUROIMMUN). In no case of positive reaction, the follow-up sample gave indications of seroconversion.

TABLE 1

|  | EURO-LINE-WB IgM | His-Cys-m-OspC$_{VS461}$ SEQ ID NO: 2 | His-m-OspC$_{VS461}$ SEQ ID NO: 1 | recomline *Borrelia* IgM *Borrelia afzelii* |
|---|---|---|---|---|
|  | n | Anti-OspC IgM | | |
| Early phase [n] | 20 | 17 | 17 | 19 |
| Sensitivity [%] | 20 | 85 | 85 | 95 |
| Healthy pregnant women [n] | 50 | 2 | 2 | 8 |
| | | | 6 | |
| Healthy blood donors [n] | 25 | 4 | 4 | 9 |
| | | | 7 | |
| Specificity [%] | 75 | 92 | 92 | 77.3 |
| | | | 82.7 | |
| Diagnostic accuracy [%] | 100 | 90.5 | 90.5 | 81.1 |
| | | | 83.2 | |

Results:

The results are summarized by way of example for OspC from *B. afzelii* in Table 1.

A large proportion of the sera of patients in an early phase of *Borrelia* infection contain IgM antibodies against OspC. In the study, the western blot with the native OspC originating from *B. afzelii* and the line blot with His-Cys-m-OspC$_{VS461}$ have virtually equivalent sensitivities and specificities and at the same time the highest diagnostic accuracies. The line blot with the variant His-m-OspC$_{VS461}$ and the recombinant OspC from *B. afzelii* on the recomBlot *Borrelia* IgM, in contrast, are distinguished above all by non-specific reactions in the healthy persons.

Example 4

Analysis of the Recombinant OspC Variants

In accordance with Example 2, the various purified OspC variants are separated by SDS-PAGE. In this context, the separation is carried out both under non-reducing conditions, under reducing conditions in the presence of dithiothreitol (DTT) and under alkylating conditions in the presence of iodoacetamide after DTT reduction. Thereafter, a western blot is carried out in accordance with Example 1. In parallel with the monoclonal antibodies against the His-tag described in Example 1, anti-OspC IgM positive sera are also incubated in a 1:200 dilution in accordance with Example 3. In the case of human sera, a conjugate of anti-human IgM and alkaline phosphatase (EUROIMMUN) diluted 1:10 in "universal buffer" is used in the second incubation step.

Results:

The separation under reducing and alkylating conditions, both after Ponceau S staining and after detection of the His-tag in accordance with Example 1, in each case leads to bands corresponding to a size of about 23-25 kDa. This also applies to the variants His-m-OspC$_{VS461}$ (SEQ ID NO:1), His-m-OspC$_{20047}$ (SEQ ID NO:4) and His-m-OspC$_{B31}$ (SEQ ID NO:7) under non-reducing conditions. In contrast, in the case of the variants His-Cys-m-OspC$_{VS461}$ (SEQ ID NO:2), His-Cys-m-OspC$_{20047}$ (SEQ ID NO:5) and His-Cys-m-OspC$_{B31}$ (SEQ ID NO:8), in each case two bands are present at 23-25 and 45-50 kDa, which are each stained approximately with the same intensity. These results indicate that the variants His-Cys-m-OspC$_{VS461}$, His-Cys-m-OspC$_{20047}$ and His-Cys-m-OspC$_{B31}$ are each present as dimmers, in which in each case two monomers are linked to one another via disulphide bridges (see FIG. 2).

After incubation with human sera, the distribution of the bands in the particular variants is identical. It is striking, however, that the bands at 45-50 kDa are in each case stained considerably more intensively than the bands at 23-25 kDa. The different colour intensities after direct staining by Ponceau S and immunological staining after incubation with human sera indicate that the dimers in each case have higher specific reactivities than the monomers (see FIG. 2).

Example 5

Preparation of Heterodimers

Aliquots of two of the OspC dimer variants purified in accordance with Example 2, e.g. His-m-Cys-OspC$_{VS461}$ and His-m-Cys-OspC$_{20047}$ are mixed with one another in equal portions. An aliquot of the mixture is stored for analysis. The remainder is reduced by addition of DTT and the success of the reduction is checked by non-reducing SDS-PAGE and western blot in accordance with Example 4. The mixture is then freed from DTT by exhaustive dialysis against 20 mM Tris-HCl pH 8.5 and compressed air is passed through for 24 hours through a pipette tip in order to create an oxidative medium. The mixture is finally analysed by non-reducing isoelectric focussing between pH 6 and 9 with the ZoomRunner system (Invitrogen) in accordance with the manufacturer's instructions, subsequent reducing SDS-PAGE and western blot. The two individual OspC dimers and the mixture before addition of DTT are analysed for comparison.

Results:

His-m-Cys-OspC$_{VS461}$ has a spot corresponding to approx. pH 7.5 and 24 kDa, His-m-OspC$_{20047}$ on the other hand corresponding to approx. pH 6.5 and 24 kDa. The mixture of His-m-OspC$_{VS461}$ and His-m-OspC$_{20047}$ before reduction has two spots corresponding to approx. pH 7.5/24 kDa and pH 6.5/24 kDa. In contrast, the reduced and subsequently air-oxidized mixture has three spots corresponding to approx. pH 7.5/24 kDa, pH 6.8/24 kDa and pH 6.5/24 kDa. The results indicate that heterodimers are at least partly present.

Example 6

Immunogenicity of OspC Dimers with Disulphide Bridges

The proteins His-m-OspC$_{VS461}$ and His-Cys-m-OspC$_{VS461}$ purified in accordance with Example 2 were injected subcutaneously without an adjuvant into 10 female C3H/He mice, respectively, aged from four to six weeks for the first time and then at an interval of 14, 28 and 42 days in portions of in each case 100 µg per dose. Further 10 mice are injected with 0.9% (w/v) saline solution as a control, respectively. Blood is taken from all animals on the day of the first injection and then after 24, 38, 52 and 66 days. OspC-specific antibodies are determined in a 1:1,000 dilution of the particular serum with the aid of an anti-*Borrelia* IgM ELISA (EUROIMMUN), in which the conjugate for detection of bound human antibodies is exchanged for a conjugate, diluted 1:2,000 in conjugate dilution buffer (EUROIMMUN), for detection of bound murine antibodies of the IgG class (Dianova). The mean (MW) and standard deviation ($\sigma$) of the results of in each case 10 animals treated in the same way are determined.

To check the specificity of the immune response, the 30 serum samples from the day of the last removal of blood are incubated on EUROLINE-WB strips (EUROIMMUN) in a 1:500 dilution and the bound murine antibodies are detected in accordance with experiment 1.

Results:

The results are given as extinction at 450 nm and are summarized in Table 2.

TABLE 2

|  |  | Day | | | | | | | | | |
|---|---|---|---|---|---|---|---|---|---|---|---|
|  |  | 0 | | 24 | | 38 | | 52 | | 66 | |
| Antigen | n | MW | $\sigma$ | MW | $\sigma$ | MW | $\sigma$ | MW | $\sigma$ | MW | $\sigma$ |
| 0.9% (w/v) NaCl solution | 10 | 0.015 | 0.002 | 0.019 | 0.004 | 0.019 | 0.006 | 0.014 | 0.002 | 0.024 | 0.005 |
| His-m-OspC$_{VS461}$ | 10 | 0.014 | 0.003 | 0.017 | 0.003 | 0.069 | 0.114 | 0.722 | 0.986 | 2.195 | 1.518 |
| His-m-Cys-OspC$_{VS461}$ | 10 | 0.014 | 0.002 | 0.036 | 0.024 | 1.043 | 0.995 | 1.892 | 1.288 | 3.868 | 0.202 |

It is found that considerably faster and higher measurement values are generated if the animals have been immunized with the variant His-m-Cys-OspC$_{VS461}$. It is furthermore found that at the end of the immunization programme, all the sera of animals immunized with the variant His-m-Cys-OspC$_{VS461}$ generate high measurement values close to the mean. In contrast, very low or low measurement values in some of the animals which were immunized with the variant His-m-OspC$_{VS461}$ indicate that the immunization in these animals did not lead to a substantial antibody titre.

The incubation on EUROLINE-WB strips shows that all the sera which generate an increased extinction ($E_{450\ nm} \geq$ 0.3) in ELISA generate a band at the migration site of the OspC. In this context, the band intensity approximately correlates with the extinction.

The two results taken together suggest that the mice which were immunized with the variant His-m-Cys-OspC$_{VS461}$ generate antibodies faster than after immunization with the variant His-m-OspC$_{VS461}$, and that higher antibody concentrations are achieved at the end of the immunization.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

LITERATURE LIST

1. Cutler S J, Wright D J: Comparison of immunofluorescence and enzyme linked immunosorbent assays for diagnosing Lyme disease. J Clin Pathol 42:869-871 (1989).
2. Earnhart C G, Buckles E L, Dumler J S, Marconi R T: Demonstration of OspC type diversity in invasive human lyme disease isolates and identification of previously uncharacterized epitopes that define the specificity of the OspC murine antibody response. Infect Immun 73:7869-7877 (2005).
3. Eicken C, Sharma V, Klabunde T, Owens R T, Pikas D S, Hook M, Sacchettini J C: Crystal structure of Lyme disease antigen outer surface protein C from *Borrelia burgdorferi*. J Biol Chem 276:10010-10015 (2001).
4. Fister R D, Weymouth L A, McLaughlin J C, Ryan R W, Tilton R C: Comparative evaluation of three products for the detection of *Borrelia burgdorferi* antibody in human serum. J Clin Microbiol 27:2834-2837 (1989).
5. Fuchs R, Jauris S, Lottspeich F, Preac-Mursic V, Wilske B, Soutschek E: Molecular analysis and expression of a *Borrelia burgdorferi* gene encoding a 22 kDa protein (pC) in *Escherichia coli*. Mol Microbiol 6:503-509 (1992).
6. Hagman K E, Landenne P, Popova T G, Porcella S F, Akins D R, Radolf J D, Norgard M V: Decorin-binding protein of *Borrelia* burgdorferi is encoded within a two-gene operon and is protective in the murine model of Lyme borreliosis. Infect Immun 66:2674-2683 (1998).
7. Hansen K, Hindersson P, Pedersen N S: Measurement of antibodies to the *Borrelia* burgdorferi flagellum improves serodiagnosis in Lyme disease. J Clin Microbiol 26:338-346 (1988).
8. Hauser U, Lehnert G, Wilske B: Diagnostic value of proteins of three *Borrelia* species (*Borrelia burgdorferi* sensu lato) and implications for development and use of recombinant antigens for serodiagnosis of Lyme borreliosis in Europe. Clin Diagn Lab Immunol 5:456-462 (1998).
9. Hyde J A, Trzeciakowski J P, Skare J T: *Borrelia burgdorferi* alters its gene expression and antigenic profile in response to CO2 levels. J Bacteriol 189:437-445 (2007).
10. Kumaran D, Eswaramoorthy S, Luft B J, Koide S, Dunn J J, Lawson C L, Swaminathan S: Crystal structure of outer surface protein C (OspC) from the Lyme disease spirochete, *Borrelia burgdorferi*. EMBO J 20:971-978 (2001).
11. Lawrenz M B, Hardham J M, Owens R T, Nowakowski J, Steere A C, Wormser G P, Norris S J: Human antibody responses to VIsE antigenic variation protein of *Borrelia burgdorferi*. J Clin Microbiol 37:3997-4004 (1999).
12. Mathiesen M J, Christiansen M, Hansen K, Holm A, Asbrink E, Theisen M: Peptide-based OspC enzyme-linked immunosorbent assay for serodiagnosis of Lyme borreliosis. J Clin Microbiol 36:3474-3479 (1998a).
13. Mathiesen M J, Holm A, Christiansen M, Blom J, Hansen K, Ostergaard S, Theisen M: The dominant epitope of *Borrelia garinii* outer surface protein C recognized by sera from patients with neuroborreliosis has a surface-exposed conserved structural motif. Infect Immun 66:4073-4079 (1998b).
14. Norris S J, Carter C J, Howell J K, Barbour A G: Low-passage-associated proteins of *Borrelia burgdorferi* B31: characterization and molecular cloning of OspD, a surface-exposed, plasmid-encoded lipoprotein. Infect Immun 60:4662-4672 (1992).
15. Pollack R J, Telford S R, III, Spielman A: Standardization of medium for culturing Lyme disease spirochetes. J Clin Microbiol 31:1251-1255 (1993).
16. Ruzic-Sabljic E, Strle F: Comparison of growth of *Borrelia afzelii, B. garinii*, and *B. burgdorferi* sensu stricto in MKP and BSK-II medium. Int J Med Microbiol 294:407-412 (2004).
17. Seshu J, Boylan J A, Gherardini F C, Skare J T: Dissolved oxygen levels alter gene expression and antigen profiles in *Borrelia burgdorferi*. Infect Immun 72:1580-1586 (2004).
18. Wilske B, Fingerle V: Lyme-Borreliose Diagnostik (2005).
19. Wilske B, Jauris-Heipke S, Lobentanzer R, Pradel I, Preac-Mursic V, Rossler D, Soutschek E, Johnson R C: Phenotypic analysis of outer surface protein C (OspC) of *Borrelia burgdorferi* sensu lato by monoclonal antibodies: relationship to genospecies and OspA serotype. J Clin Microbiol 33:103-109 (1995).
20. Wilske B, Preac-Mursic V, Jauris S, Hofmann A, Pradel I, Soutschek E, Schwab E, Will G, Wanner G: Immunological and molecular polymorphisms of OspC, an immunodominant major outer surface protein of *Borrelia burgdorferi*. Infect Immun 61:2182-2191 (1993).
21. Wu H C, Tokunaga M: Biogenesis of lipoproteins in bacteria. Curr Top Microbiol Immunol 125:127-157 (1986).
22. Yang X, Popova T G, Goldberg M S, Norgard M V: Influence of cultivation media on genetic regulatory patterns in *Borrelia burgdorferi*. Infect Immun 69:4159-4163 (2001).
23. WO 9742221
24. EP1741718

The invention claimed is:

1. A vaccine against a *Borrelia* infection comprising a protein, said protein comprising a first OspC polypeptide comprising one or more cysteines and a second OspC polypeptide comprising one or more cysteines, wherein the first OspC polypeptide is linked to the second OspC polypeptide via a disulphide bridge formed between the most N-terminal cysteines in the first and second OspC polypeptides, and wherein both the first and second OspC polypeptides comprise at least one epitope that is specifically recognized by antibodies against OspC from *Borrelia*, the epitope comprising at least 10 contiguous amino acids from SEQ ID NO:3, SEQ ID NO:6, or SEQ ID NO:9.

2. The vaccine according to claim 1, wherein both the first and second OspC polypeptides have an amino acid identity of at least 90% with SEQ ID NO:3, SEQ ID NO:6 or SEQ ID NO:9.

3. The vaccine according to claim 1, wherein the at least 10 contiguous amino acids from SEQ ID NO:3, SEQ ID NO:6 or SEQ ID NO:9 are the 10 C-terminal amino acids of these sequences and said at least 10 contiguous amino acids are in the C-terminal location of the OspC polypeptide.

4. The vaccine according to claim 1, wherein the first OspC polypeptide, the second OspC polypeptide, or both the first and second OspC polypeptides do not comprise any recognition sequence for an acylation.

5. The vaccine according to claim 1, wherein the disulphide bridge is formed by linking of a cysteine which is not more than 30 amino acid positions away from the N-terminus of the first OspC polypeptide, the second OspC polypeptide, or both the first and second OspC polypeptides.

6. The vaccine according to claim 1, wherein the first OspC polypeptide, the second OspC polypeptide, or both the first and second polypeptides comprise a sequence according to SEQ ID NO:2, SEQ ID NO:5 or SEQ ID NO:8.

7. The vaccine according to claim 1, wherein by means of the disulphide bridge a homodimer of two identical OspC polypeptides is formed.

8. The vaccine according to claim 1, wherein the recognition of the polypeptide by antibodies against OspC from *Borrelia* would be reduced by bringing the protein into contact with at least one thiol-containing reagent.

9. The vaccine according to claim 1, wherein by means of the disulphide bridge a heterodimer of different OspC polypeptides is formed.

10. The vaccine according to claim 1, wherein the recognition of the polypeptide by antibodies against OspC from *Borrelia* would be reduced by bringing the protein into contact with at least one thiol-containing reagent in combination with an alkyl halide.

* * * * *

SEQUENCE LISTING

<160> NUMBER OF SEQ ID NOS: 24

<210> SEQ ID NO 1
<211> LENGTH: 203
<212> TYPE: PRT
<213> ORGANISM: Artificial
<220> FEATURE:
<223> OTHER INFORMATION: Generated by genetic engineering.

<400> SEQUENCE: 1

Met Ser His His His His His His His Ser Met Gly Asn Asn Ser
1               5                   10                  15

Gly Lys Gly Gly Asp Ile Ala Ser Thr Asn Pro Asp Glu Ser Ala Lys
            20                  25                  30

Gly Pro Asn Leu Thr Glu Ile Ser Lys Lys Ile Thr Asp Ser Asn Ala

```
                35                  40                  45
Val Val Leu Ala Val Lys Glu Val Glu Ala Leu Leu Ser Ser Ile Asp
 50                  55                  60

Glu Leu Ala Lys Thr Ile Gly Lys Lys Ile Glu Ala Asn Gly Leu Gly
 65                  70                  75                  80

Asn Glu Ala Asp Lys Asn Gly Ser Leu Leu Ala Gly Ala Tyr Ala Ile
                 85                  90                  95

Ser Thr Leu Ile Lys Gln Lys Leu Asp Gly Leu Lys Gly Leu Glu Gly
                100                 105                 110

Leu Asn Lys Glu Ile Ala Glu Ala Lys Lys Cys Ser Glu Ala Phe Thr
                115                 120                 125

Lys Lys Leu Gln Asp Ser Asn Ala Asp Leu Gly Lys His Asn Ala Thr
130                 135                 140

Asp Ala Asp Ser Lys Glu Ala Ile Leu Lys Thr Asn Gly Thr Lys Thr
145                 150                 155                 160

Lys Gly Ala Lys Glu Leu Glu Glu Leu Phe Lys Ser Val Glu Ser Leu
                165                 170                 175

Ser Lys Ala Ala Lys Glu Ala Leu Ser Asn Ser Val Lys Glu Leu Thr
                180                 185                 190

Ser Pro Val Val Ala Glu Ser Pro Lys Lys Pro
                195                 200

<210> SEQ ID NO 2
<211> LENGTH: 203
<212> TYPE: PRT
<213> ORGANISM: Artificial
<220> FEATURE:
<223> OTHER INFORMATION: Generated by genetic engineering.

<400> SEQUENCE: 2

Met Ser His His His His His His His Ser Met Cys Asn Asn Ser
 1               5                  10                  15

Gly Lys Gly Gly Asp Ile Ala Ser Thr Asn Pro Asp Glu Ser Ala Lys
                 20                  25                  30

Gly Pro Asn Leu Thr Glu Ile Ser Lys Lys Ile Thr Asp Ser Asn Ala
                 35                  40                  45

Val Val Leu Ala Val Lys Glu Val Glu Ala Leu Leu Ser Ser Ile Asp
 50                  55                  60

Glu Leu Ala Lys Thr Ile Gly Lys Lys Ile Glu Ala Asn Gly Leu Gly
 65                  70                  75                  80

Asn Glu Ala Asp Lys Asn Gly Ser Leu Leu Ala Gly Ala Tyr Ala Ile
                 85                  90                  95

Ser Thr Leu Ile Lys Gln Lys Leu Asp Gly Leu Lys Gly Leu Glu Gly
                100                 105                 110

Leu Asn Lys Glu Ile Ala Glu Ala Lys Lys Cys Ser Glu Ala Phe Thr
                115                 120                 125

Lys Lys Leu Gln Asp Ser Asn Ala Asp Leu Gly Lys His Asn Ala Thr
130                 135                 140

Asp Ala Asp Ser Lys Glu Ala Ile Leu Lys Thr Asn Gly Thr Lys Thr
145                 150                 155                 160

Lys Gly Ala Lys Glu Leu Glu Glu Leu Phe Lys Ser Val Glu Ser Leu
                165                 170                 175

Ser Lys Ala Ala Lys Glu Ala Leu Ser Asn Ser Val Lys Glu Leu Thr
                180                 185                 190

Ser Pro Val Val Ala Glu Ser Pro Lys Lys Pro
                195                 200
```

-continued

<210> SEQ ID NO 3
<211> LENGTH: 191
<212> TYPE: PRT
<213> ORGANISM: Borrelia afzelii VS461

<400> SEQUENCE: 3

Cys Asn Asn Ser Gly Lys Gly Gly Asp Ile Ala Ser Thr Asn Pro Asp
1               5

```
                130                 135                 140
Asp Asp Glu Ala Lys Lys Ala Ile Leu Lys Thr Asn Val Asp Lys Thr
145                 150                 155                 160

Lys Gly Ala Glu Glu Leu Glu Lys Leu Phe Lys Ser Val Glu Ser Leu
                165                 170                 175

Ser Lys Ala Ala Gln Glu Ala Leu Thr Asn Ser Val Lys Glu Leu Thr
                180                 185                 190

Asn Pro Val Val Ala Glu Thr Pro Lys Lys Pro
                195                 200

<210> SEQ ID NO 5
<211> LENGTH: 203
<212> TYPE: PRT
<213> ORGANISM: Artificial
<220> FEATURE:
<223> OTHER INFORMATION: Generated by genetic engineering.

<400> SEQUENCE: 5

Met Ser His His His His His His Ser Met Cys Asn Asn Ser
1               5                   10                  15

Gly Gly Asp Thr Ala Ser Thr Asn Pro Asp Glu Ser Val Lys Gly Pro
                20                  25                  30

Asn Leu Thr Glu Ile Ser Lys Lys Ile Thr Asp Ser Asn Ala Phe Val
                35                  40                  45

Leu Ala Val Lys Glu Val Glu Ala Leu Ile Ser Ser Ile Asp Glu Leu
        50                  55                  60

Ala Lys Ala Ile Gly Gln Arg Ile Gln Gln Asn Gly Leu Val Ala Asp
65                  70                  75                  80

Ala Gly His Asn Ser Ala Leu Leu Ala Gly Ala His Glu Ile Ser Ile
                85                  90                  95

Leu Ile Thr Gln Lys Leu Asp Gly Leu Lys Gly Leu Glu Gly Leu Lys
                100                 105                 110

Ala Glu Ile Ala Glu Ala Lys Lys Tyr Ser Glu Ala Phe Thr Lys Lys
            115                 120                 125

Leu Lys Asp Asn His Ala Gln Leu Gly Ile Gln Asn Gly Ala Ser Leu
        130                 135                 140

Asp Asp Glu Ala Lys Lys Ala Ile Leu Lys Thr Asn Val Asp Lys Thr
145                 150                 155                 160

Lys Gly Ala Glu Glu Leu Glu Lys Leu Phe Lys Ser Val Glu Ser Leu
                165                 170                 175

Ser Lys Ala Ala Gln Glu Ala Leu Thr Asn Ser Val Lys Glu Leu Thr
                180                 185                 190

Asn Pro Val Val Ala Glu Thr Pro Lys Lys Pro
                195                 200

<210> SEQ ID NO 6
<211> LENGTH: 191
<212> TYPE: PRT
<213> ORGANISM: Borrelia garinii 20047

<400> SEQUENCE: 6

Cys Asn Asn Ser Gly Gly Asp Thr Ala Ser Thr Asn Pro Asp Glu Ser
1               5                   10                  15

Val Lys Gly Pro Asn Leu Thr Glu Ile Ser Lys Lys Ile Thr Asp Ser
                20                  25                  30

Asn Ala Phe Val Leu Ala Val Lys Glu Val Glu Ala Leu Ile Ser Ser
            35                  40                  45
```

```
Ile Asp Glu Leu Ala Lys Ala Ile Gly Gln Arg Ile Gln Gln Asn Gly
         50                  55                  60

Leu Val Ala Asp Ala Gly His Asn Ser Ala Leu Leu Ala Gly Ala His
 65                  70                  75                  80

Glu Ile Ser Ile Leu Ile Thr Gln Lys Leu Asp Gly Leu Lys Gly Leu
                 85                  90                  95

Glu Gly Leu Lys Ala Glu Ile Ala Glu Ala Lys Lys Tyr Ser Glu Ala
             100                 105                 110

Phe Thr Lys Lys Leu Lys Asp Asn His Ala Gln Leu Gly Ile Gln Asn
             115                 120                 125

Gly Ala Ser Leu Asp Asp Glu Ala Lys Lys Ala Ile Leu Lys Thr Asn
         130                 135                 140

Val Asp Lys Thr Lys Gly Ala Glu Glu Leu Glu Lys Leu Phe Lys Ser
145                 150                 155                 160

Val Glu Ser Leu Ser Lys Ala Ala Gln Glu Ala Leu Thr Asn Ser Val
                 165                 170                 175

Lys Glu Leu Thr Asn Pro Val Val Ala Glu Thr Pro Lys Lys Pro
                 180                 185                 190

<210> SEQ ID NO 7
<211> LENGTH: 204
<212> TYPE: PRT
<213> ORGANISM: Artificial
<220> FEATURE:
<223> OTHER INFORMATION: Generated by genetic engineering.

<400> SEQUENCE: 7

Met Ser His His His His His His Ser Met Gly Asn Asn Ser
  1               5                  10                  15

Gly Lys Asp Gly Asn Thr Ser Ala Asn Ser Ala Asp Glu Ser Val Lys
             20                  25                  30

Gly Pro Asn Leu Thr Glu Ile Ser Lys Lys Ile Thr Asp Ser Asn Ala
         35                  40                  45

Val Leu Leu Ala Val Lys Glu Val Glu Ala Leu Leu Ser Ser Ile Asp
 50                  55                  60

Glu Ile Ala Ala Lys Ala Ile Gly Lys Lys Ile His Gln Asn Asn Gly
 65                  70                  75                  80

Leu Asp Thr Glu Asn Asn His Asn Gly Ser Leu Leu Ala Gly Ala Tyr
                 85                  90                  95

Ala Ile Ser Thr Leu Ile Lys Gln Lys Leu Asp Gly Leu Lys Asn Glu
             100                 105                 110

Gly Leu Lys Glu Lys Ile Asp Ala Ala Lys Lys Cys Ser Glu Thr Phe
             115                 120                 125

Thr Asn Lys Leu Lys Glu Lys His Thr Asp Leu Gly Lys Glu Gly Val
         130                 135                 140

Thr Asp Ala Asp Ala Lys Glu Ala Ile Leu Lys Thr Asn Gly Thr Lys
145                 150                 155                 160

Thr Lys Gly Ala Glu Glu Leu Gly Lys Leu Phe Glu Ser Val Glu Val
                 165                 170                 175

Leu Ser Lys Ala Ala Lys Glu Met Leu Ala Asn Ser Val Lys Glu Leu
             180                 185                 190

Thr Ser Pro Val Val Ala Glu Ser Pro Lys Lys Pro
             195                 200

<210> SEQ ID NO 8
<211> LENGTH: 204
<212> TYPE: PRT
```

```
<213> ORGANISM: Artificial
<220> FEATURE:
<223> OTHER INFORMATION: Generated by genetic engineering.

<400> SEQUENCE: 8

Met Ser His His His His His His Ser Met Cys Asn Asn Ser
1               5                   10                  15

Gly Lys Asp Gly Asn Thr Ser Ala Asn Ser Ala Asp Glu Ser Val Lys
            20                  25                  30

Gly Pro Asn Leu Thr Glu Ile Ser Lys Lys Ile Thr Asp Ser Asn Ala
        35                  40                  45

Val Leu Leu Ala Val Lys Glu Val Glu Ala Leu Leu Ser Ser Ile Asp
50                  55                  60

Glu Ile Ala Ala Lys Ala Ile Gly Lys Lys Ile His Gln Asn Asn Gly
65                  70                  75                  80

Leu Asp Thr Glu Asn Asn His Asn Gly Ser Leu Leu Ala Gly Ala Tyr
                85                  90                  95

Ala Ile Ser Thr Leu Ile Lys Gln Lys Leu Asp Gly Leu Lys Asn Glu
            100                 105                 110

Gly Leu Lys Glu Lys Ile Asp Ala Ala Lys Lys Cys Ser Glu Thr Phe
        115                 120                 125

Thr Asn Lys Leu Lys Glu Lys His Thr Asp Leu Gly Lys Glu Gly Val
    130                 135                 140

Thr Asp Ala Asp Ala Lys Glu Ala Ile Leu Lys Thr Asn Gly Thr Lys
145                 150                 155                 160

Thr Lys Gly Ala Glu Glu Leu Gly Lys Leu Phe Glu Ser Val Glu Val
                165                 170                 175

Leu Ser Lys Ala Ala Lys Glu Met Leu Ala Asn Ser Val Lys Glu Leu
            180                 185                 190

Thr Ser Pro Val Val Ala Glu Ser Pro Lys Lys Pro
        195                 200

<210> SEQ ID NO 9
<211> LENGTH: 192
<212> TYPE: PRT
<213> ORGANISM: Borrelia burgdorferi B31

<400> SEQUENCE: 9

Cys Asn Asn Ser Gly Lys Asp Gly Asn Thr Ser Ala Asn Ser Ala Asp
1               5                   10                  15

Glu Ser Val Lys Gly Pro Asn Leu Thr Glu Ile Ser Lys Lys Ile Thr
            20                  25                  30

Asp Ser Asn Ala Val Leu Leu Ala Val Lys Glu Val Glu Ala Leu Leu
        35                  40                  45

Ser Ser Ile Asp Glu Ile Ala Ala Lys Ala Ile Gly Lys Lys Ile His
    50                  55                  60

Gln Asn Asn Gly Leu Asp Thr Glu Asn Asn His Asn Gly Ser Leu Leu
65                  70                  75                  80

Ala Gly Ala Tyr Ala Ile Ser Thr Leu Ile Lys Gln Lys Leu Asp Gly
                85                  90                  95

Leu Lys Asn Glu Gly Leu Lys Glu Lys Ile Asp Ala Ala Lys Lys Cys
            100                 105                 110

Ser Glu Thr Phe Thr Asn Lys Leu Lys Glu Lys His Thr Asp Leu Gly
        115                 120                 125

Lys Glu Gly Val Thr Asp Ala Asp Ala Lys Glu Ala Ile Leu Lys Thr
    130                 135                 140
```

```
Asn Gly Thr Lys Thr Lys Gly Ala Glu Glu Leu Gly Lys Leu Phe Glu
145                 150                 155                 160

Ser Val Glu Val Leu Ser Lys Ala Ala Lys Glu Met Leu Ala Asn Ser
            165                 170                 175

Val Lys Glu Leu Thr Ser Pro Val Val Ala Glu Ser Pro Lys Lys Pro
        180                 185                 190

<210> SEQ ID NO 10
<211> LENGTH: 609
<212> TYPE: DNA
<213> ORGANISM: Artificial
<220> FEATURE:
<223> OTHER INFORMATION: Generated by genetic engineering.

<400> SEQUENCE: 10
atgagccatc atcatcatca tcatcatcat tccatgggta ataattcagg gaaaggtggg    60
gatattgcat ctactaatcc tgatgagtct gcgaaaggac ctaatcttac agaaataagc   120
aaaaaaatta cagattccaa tgcagttgta ctagctgtga agaagttga ggctttgctt    180 tcatctatag atgaacttgc taaaactatt ggtaaaaaaa tagaggcaaa tggtttgggt   240
aacgaagcgg ataaaacgg atcattatta gcaggagcct atgcaatatc aaccctaata   300
aaacaaaaat tagatggatt gaaaggtcta gaaggattaa ataaagaaat tgcggaggcc   360
aagaaatgtt ccgaagcatt tactaaaaag ctacaagata gtaacgcaga tcttggaaaa   420
cataatgcta ctgatgctga ttcaaaagaa gcaattttga aaacaaatgg gactaaaact   480
aagggtgcta agaacttga agagttgttt aaatcagtag aaagcttgtc aaaagcagct    540
aaagaagcat taagtaattc agttaaagag cttacaagcc ctgttgtggc agaaagtcca   600
aaaaaacct                                                          609

<210> SEQ ID NO 11
<211> LENGTH: 609
<212> TYPE: DNA
<213> ORGANISM: Artificial
<220> FEATURE:
<223> OTHER INFORMATION: Generated by genetic engineering.

<400> SEQUENCE: 11
atgagccatc atcatcatca tcatcatcat tccatgtgta ataattcagg gaaaggtggg    60
gatattgcat ctactaatcc tgatgagtct gcgaaaggac ctaatcttac agaaataagc   120
aaaaaaatta cagattccaa tgcagttgta ctagctgtga agaagttga ggctttgctt    180 tcatctatag atgaacttgc taaaactatt ggtaaaaaaa tagaggcaaa tggtttgggt   240
aacgaagcgg ataaaacgg atcattatta gcaggagcct atgcaatatc aaccctaata   300
aaacaaaaat tagatggatt gaaaggtcta gaaggattaa ataaagaaat tgcggaggcc   360
aagaaatgtt ccgaagcatt tactaaaaag ctacaagata gtaacgcaga tcttggaaaa   420
cataatgcta ctgatgctga ttcaaaagaa gcaattttga aaacaaatgg gactaaaact   480
aagggtgcta agaacttga agagttgttt aaatcagtag aaagcttgtc aaaagcagct    540
aaagaagcat taagtaattc agttaaagag cttacaagcc ctgttgtggc agaaagtcca   600
aaaaaacct                                                          609

<210> SEQ ID NO 12
<211> LENGTH: 609
<212> TYPE: DNA
<213> ORGANISM: Artificial
<220> FEATURE:
<223> OTHER INFORMATION: Generated by genetic engineering.
```

<400> SEQUENCE: 12

```
atgagccatc atcatcatca tcatcatcat tccatgggta ataattcagg tgggatact       60
gcatctacta atcctgatga atctgttaag gggcctaatc ttacagaaat aagcaaaaaa     120
attacagatt ctaatgcatt tgtactggct gtgaaagaag ttgaggcttt gatctcatct    180
atagatgaac ttgctaaagc tattggtcaa agaatacaac aaaatggttt agttgctgat    240
gcgggtcaca acagcgcatt gttagcagga gcccatgaaa tatcaatcct aataacacaa    300
aaattagatg gattaaaagg tttagaagga ttaaaagcag agattgcaga agctaagaaa    360
tattctgaag catttactaa aaaactaaaa gataatcatg cacagcttgg tatacagaat    420
ggtgcttctc ttgatgatga ggcaaaaaaa gctattttaa aaacaaatgt ggacaaaacc    480
aagggtgctg aagagcttga aaagttattt aaatcagtag aaagcttgtc aaaagcagcg    540
caagaagcac taactaattc agttaaagag cttacaaatc ctgttgtggc agaaactcca    600
aaaaaacct                                                             609
```

<210> SEQ ID NO 13
<211> LENGTH: 609
<212> TYPE: DNA
<213> ORGANISM: Artificial
<220> FEATURE:
<223> OTHER INFORMATION: Generated by genetic engineering.

<400> SEQUENCE: 13

```
atgagccatc atcatcatca tcatcatcat tccatgtgta ataattcagg tgggatact      60
gcatctacta atcctgatga atctgttaag gggcctaatc ttacagaaat aagcaaaaaa    120
attacagatt ctaatgcatt tgtactggct gtgaaagaag ttgaggcttt gatctcatct    180
atagatgaac ttgctaaagc tattggtcaa agaatacaac aaaatggttt agttgctgat    240
gcgggtcaca acagcgcatt gttagcagga gcccatgaaa tatcaatcct aataacacaa    300
aaattagatg gattaaaagg tttagaagga ttaaaagcag agattgcaga agctaagaaa    360
tattctgaag catttactaa aaaactaaaa gataatcatg cacagcttgg tatacagaat    420
ggtgcttctc ttgatgatga ggcaaaaaaa gctattttaa aaacaaatgt ggacaaaacc    480
aagggtgctg aagagcttga aaagttattt aaatcagtag aaagcttgtc aaaagcagcg    540
caagaagcac taactaattc agttaaagag cttacaaatc ctgttgtggc agaaactcca    600
aaaaaacct                                                             609
```

<210> SEQ ID NO 14
<211> LENGTH: 612
<212> TYPE: DNA
<213> ORGANISM: Artificial
<220> FEATURE:
<223> OTHER INFORMATION: Generated by genetic engineering.

<400> SEQUENCE: 14

```
atgagccatc atcatcatca tcatcatcat tccatgggta ataattcagg gaaagatggg     60
aatacatctg caaattctgc tgatgagtct gttaagggc ctaatcttac agaaataagt    120
aaaaaaatta cggattctaa tgcggtttta cttgctgtga agaggttga agcgttgctg    180
tcatctatag atgaaattgc tgctaaagct attggtaaaa aatacacca aataatggt     240
ttggataccg aaaataatca caatggatca ttgttagcgg gagcttatgc aatatcaacc    300
ctaataaaac aaaaattaga tggattgaaa aatgaaggat taaggaaaa aattgatgcg    360
gctaagaaat gttctgaaac atttactaat aaattaaaag aaaaacacac agatcttggt    420
```

```
aaagaaggtg ttactgatgc tgatgcaaaa gaagccattt taaaaacaaa tggtactaaa        480
actaaaggtg ctgaagaact tggaaaatta tttgaatcag tagaggtctt gtcaaaagca        540
gctaaagaga tgcttgctaa ttcagttaaa gagcttacaa gccctgttgt ggcagaaagt        600
ccaaaaaaac ct                                                            612

<210> SEQ ID NO 15
<211> LENGTH: 612
<212> TYPE: DNA
<213> ORGANISM: Artificial
<220> FEATURE:
<223> OTHER INFORMATION: Generated by genetic engineering.

<400> SEQUENCE: 15
atgagccatc atcatcatca tcatcatcat tccatgtgta ataattcagg gaaagatggg         60
aatacatctg caaattctgc tgatgagtct gttaaagggc ctaatcttac agaaataagt        120
aaaaaaatta cggattctaa tgcggtttta cttgctgtga agaggttgaa agcgttgctg        180
tcatctatag atgaaattgc tgctaaagct attggtaaaa aaatacacca aaataatggt        240
ttggataccg aaaataatca caatggatca ttgttagcgg gagcttatgc aatatcaacc        300
ctaataaaac aaaaattaga tggattgaaa atgaaggat taaggaaaa aattgatgcg         360 gctaagaaat gttctgaaac atttactaat aaattaaaag aaaaacacac agatcttggt        420
aaagaaggtg ttactgatgc tgatgcaaaa gaagccattt taaaaacaaa tggtactaaa        480
actaaaggtg ctgaagaact tggaaaatta tttgaatcag tagaggtctt gtcaaaagca        540
gctaaagaga tgcttgctaa ttcagttaaa gagcttacaa gccctgttgt ggcagaaagt        600
ccaaaaaaac ct                                                            612

<210> SEQ ID NO 16
<211> LENGTH: 31
<212> TYPE: DNA
<213> ORGANISM: Artificial
<220> FEATURE:
<223> OTHER INFORMATION: Generated by DNA synthesis.

<400> SEQUENCE: 16
tagaccatgg gtaataattc agggaaaggt g                                        31

<210> SEQ ID NO 17
<211> LENGTH: 42
<212> TYPE: DNA
<213> ORGANISM: Artificial
<220> FEATURE:
<223> OTHER INFORMATION: Generated by DNA synthesis.

<400> SEQUENCE: 17
gcagagtgcc tcgagttaag gttttttggg actttctgcc ac                            42

<210> SEQ ID NO 18
<211> LENGTH: 43
<212> TYPE: DNA
<213> ORGANISM: Artificial
<220> FEATURE:
<223> OTHER INFORMATION: Generated by DNA synthesis.

<400> SEQUENCE: 18
atatcgtctc ccatgtgcaa taattcaggg aaaggtgggg ata                           43

<210> SEQ ID NO 19
<211> LENGTH: 44
```

```
<212> TYPE: DNA
<213> ORGANISM: Artificial
<220> FEATURE:
<223> OTHER INFORMATION: Generated by DNA synthesis.

<400> SEQUENCE: 19
atatcgtctc ccatgggtaa taattcaggt ggggatactg catc          44

<210> SEQ ID NO 20
<211> LENGTH: 36
<212> TYPE: DNA
<213> ORGANISM: Artificial
<220> FEATURE:
<223> OTHER INFORMATION: Generated by DNA synthesis.

<400> SEQUENCE: 20
atactcgagt taaggttttt ttggagtttc tgccac                   36

<210> SEQ ID NO 21
<211> LENGTH: 44
<212> TYPE: DNA
<213> ORGANISM: Artificial
<220> FEATURE:
<223> OTHER INFORMATION: Generated by DNA synthesis.

<400> SEQUENCE: 21
atatcgtctc ccatgtgtaa taattcaggt ggggatactg catc          44

<210> SEQ ID NO 22
<211> LENGTH: 33
<212> TYPE: DNA
<213> ORGANISM: Artificial
<220> FEATURE:
<223> OTHER INFORMATION: Generated by DNA synthesis.

<400> SEQUENCE: 22
tagaccatgg gtaataattc agggaaagat ggg                      33

<210> SEQ ID NO 23
<211> LENGTH: 44
<212> TYPE: DNA
<213> ORGANISM: Artificial
<220> FEATURE:
<223> OTHER INFORMATION: Generated by DNA synthesis.

<400> SEQUENCE: 23
atatcgtctc ccatgtgcaa taattcaggg aaagatggga atac          44

<210> SEQ ID NO 24
<211> LENGTH: 5287
<212> TYPE: DNA
<213> ORGANISM: Artificial
<220> FEATURE:
<223> OTHER INFORMATION: Generated by genetic engineering.

<400> SEQUENCE: 24
ggggaattgt gagcggataa caattcccct ctagaaataa ttttgtttaa ctttaagaag    60
gagatatacc atgagccatc atcatcatca tcatcatcat tccatggcga tatccctcga   120
gtaagtcgag caccaccacc accaccactg agatccggct gctaacaaag cccgaaagga   180
agctgagttg gctgctgcca ccgctgagca ataactagca taaccccttg ggcctctaa    240 acgggtcttg aggggttttt tgctgaaagg aggaactata tccggattgg cgaatgggac   300
gcgccctgta gcggcgcatt aagcgcggcg ggtgtggtgg ttacgcgcag cgtgaccgct   360
acacttgcca gcgccctagc gcccgctcct ttcgctttct tcccttcctt tctcgccacg   420
```

```
ttcgccggct ttccccgtca agctctaaat cggggctcc ctttaggtt ccgatttagt      480
gctttacggc acctcgaccc caaaaaactt gattagggtg atggttcacg tagtgggcca      540
tcgccctgat agacggtttt tcgcccttg acgttggagt ccacgttctt taatagtgga       600
ctcttgttcc aaactggaac aacactcaac cctatctcgg tctattcttt tgatttataa      660
gggattttgc cgatttcggc ctattggtta aaaatgagc tgatttaaca aaaatttaac       720
gcgaatttta acaaaatatt aacgtttaca atttcaggtg cacttttcg gggaaatgtg       780
cgcggaaccc ctatttgttt attttttctaa atacattcaa atatgtatcc gctcatgaat      840
taattcttag aaaaactcat cgagcatcaa atgaaactgc aatttattca tatcaggatt      900
atcaatacca tatttttgaa aaagccgttt ctgtaatgaa ggagaaaact caccgaggca      960
gttccatagg atggcaagat cctggtatcg gtctgcgatt ccgactcgtc caacatcaat     1020
acaacctatt aatttcccct cgtcaaaaat aaggttatca agtgagaaat caccatgagt     1080
gacgactgaa tccggtgaga atggcaaaag tttatgcatt tctttccaga cttgttcaac     1140
aggccagcca ttacgctcgt catcaaaatc actcgcatca accaaaccgt tattcattcg     1200
tgattgcgcc tgagcgagac gaaatacgcg atcgctgtta aaaggacaat tacaaacagg     1260
aatcgaatgc aaccggcgca ggaacactgc cagcgcatca acaatatttt cacctgaatc     1320
aggatattct tctaatacct ggaatgctgt tttcccgggg atcgcagtgg tgagtaacca     1380
tgcatcatca ggagtacgga taaaatgctt gatggtcgga agaggcataa attccgtcag     1440
ccagtttagt ctgaccatct catctgtaac atcattggca acgctacctt tgccatgttt     1500
cagaaacaac tctggcgcat cgggcttccc atacaatcga tagattgtcg cacctgattg     1560
cccgacatta tcgcgagccc atttataccc atataaatca gcatccatgt tggaatttaa     1620
tcgcggccta gagcaagacg tttcccgttg aatatggctc ataacacccc ttgtattact     1680
gtttatgtaa gcagacagtt ttattgttca tgaccaaaat cccttaacgt gagttttcgt     1740
tccactgagc gtcagacccc gtagaaaaga tcaaggatc ttcttgagat ccttttttttc     1800
tgcgcgtaat ctgctgcttg caaacaaaaa aaccaccgct accagcggtg gtttgtttgc     1860
cggatcaaga gctaccaact ctttttccga aggtaactgg cttcagcaga gcgcagatac     1920
caaatactgt ccttctagtg tagccgtagt taggccacca cttcaagaac tctgtagcac     1980
cgcctacata cctcgctctg ctaatcctgt taccagtggc tgctgccagt ggcgataagt     2040
cgtgtcttac cgggttggac tcaagacgat agttaccgga taaggcgcag cggtcgggct     2100
gaacggggg ttcgtgcaca cagcccagct tggagcgaac gacctacacc gaactgagat     2160
acctacagcg tgagctatga gaaagcgcca cgcttcccga agggagaaag gcggacaggt     2220
atccggtaag cggcagggtc ggaacaggag agcgcacgag ggagcttcca gggggaaacg     2280
cctggtatct ttatagtcct gtcgggtttc gccacctctg acttgagcgt cgatttttgt     2340
gatgctcgtc aggggggcgg agcctatgga aaaacgccag caacgcggcc ttttacggt      2400
tcctggcctt tgctggcct tttgctcaca tgttctttcc tgcgttatcc cctgattctg      2460
tggataaccg tattaccgcc tttgagtgag ctgataccgc tcgccgcagc cgaacgaccg     2520
agcgcagcga gtcagtgagc gaggaagcgg aagagcgcct gatgcggtat tttctcctta     2580
cgcatctgtg cggtatttca caccgcatat atggtgcact ctcagtacaa tctgctctga     2640
tgccgcatag ttaagccagt atacactccg ctatcgctac gtgactgggt catggctgcg     2700
ccccgacacc cgccaacacc cgctgacgcg ccctgacggg cttgtctgct cccggcatcc     2760
gcttacagac aagctgtgac cgtctccggg agctgcatgt gtcagaggtt ttcaccgtca     2820
```

```
tcaccgaaac gcgcgaggca gctgcggtaa agctcatcag cgtggtcgtg aagcgattca   2880
cagatgtctg cctgttcatc cgcgtccagc tcgttgagtt tctccagaag cgttaatgtc   2940
tggcttctga taaagcgggc catgttaagg gcggtttttt cctgtttggt cactgatgcc   3000
tccgtgtaag ggggatttct gttcatgggg gtaatgatac cgatgaaacg agagaggatg   3060
ctcacgatac gggttactga tgatgaacat gcccggttac tggaacgttg tgagggtaaa   3120
caactggcgg tatggatgcg gcgggaccag agaaaaatca ctcagggtca atgccagcgc   3180
ttcgttaata cagatgtagg tgttccacag ggtagccagc agcatcctgc gatgcagatc   3240
cggaacataa tggtgcaggg cgctgacttc cgcgtttcca gactttacga aacacggaaa   3300
ccgaagacca ttcatgttgt tgctcaggtc gcagacgttt tgcagcagca gtcgcttcac   3360
gttcgctcgc gtatcggtga ttcattctgc taaccagtaa ggcaaccccg ccagcctagc   3420
cgggtcctca acgacaggag cacgatcatg cgcacccgtg gggccgccat gccggcgata   3480
atggcctgct tctcgccgaa acgtttggtg gcggaccag tgacgaaggc ttgagcgagg    3540
gcgtgcaaga ttccgaatac cgcaagcgac aggccgatca tcgtcgcgct ccagcgaaag   3600
cggtcctcgc cgaaaatgac ccagagcgct gccggcacct gtcctacgag ttgcatgata   3660
aagaagacag tcataagtgc ggcgacgata gtcatgcccc gcgcccaccg gaaggagctg   3720
actgggttga aggctctcaa gggcatcggt cgagatcccg tgcctaatg agtgagctaa    3780 cttacattaa ttgcgttgcg ctcactgccc gctttccagt cgggaaacct gtcgtgccag   3840
ctgcattaat gaatcggcca acgcgcgggg agaggcggtt tgcgtattgg gcgccagggt   3900
ggttttcctt ttcaccagtg agacgggcaa cagctgattg cccttcaccg cctggccctg   3960
agagagttgc agcaagcggt ccacgctggt ttgccccagc aggcgaaaat cctgtttgat   4020
ggtggttaac ggcgggatat aacatgagct gtcttcggta tcgtcgtatc ccactaccga   4080
gatatccgca ccaacgcgca gcccggactc ggtaatggcg cgcattgcgc ccagcgccat   4140
ctgatcgttg gcaaccagca tcgcagtggg aacgatgccc tcattcagca tttgcatggt   4200
ttgttgaaaa ccggacatgg cactccagtc gccttcccgt tccgctatcg gctgaatttg   4260
attgcgagtg agatatttat gccagccagc cagacgcaga cgcgccgaga cagaacttaa   4320
tgggcccgct aacagcgcga tttgctggtg acccaatgcg accagatgct ccacgcccag   4380
tcgcgtaccg tcttcatggg agaaaataat actgttgatg ggtgtctggt cagagacatc   4440
aagaaataac gccggaacat tagtgcaggc agcttccaca gcaatggcat cctggtcatc   4500
cagcggatag ttaatgatca gcccactgac gcgttgcgcg agaagattgt gcaccgccgc   4560
tttacaggct tcgacgccgc ttcgttctac catcgacacc accacgctgg cacccagttg   4620
atcggcgcga gatttaatcg ccgcgacaat ttgcgacggc gcgtgcaggg ccagactgga   4680
ggtggcaacg ccaatcagca acgactgttt gcccgccagt tgttgtgcca cgcggttggg   4740
aatgtaattc agctccgcca tcgccgcttc acttttttcc cgcgttttcg cagaaacgtg   4800
gctggcctgg ttcaccacgc gggaaacggt ctgataagag acaccggcat actctgcgac   4860
atcgtataac gttactggtt tcacattcac caccctgaat tgactctctt ccgggcgcta   4920
tcatgccata ccgcgaaagg ttttgcgcca ttcgatggtg tccgggatct cgacgctctc   4980
ccttatgcga ctcctgcatt aggaagcagc ccagtagtag gttgaggccg ttgagcaccg   5040
ccgccgcaag gaatggtgca tgcaaggaga tggcgcccaa cagtccccg gccacggggc    5100 ctgccaccat acccacgccg aaacaagcgc tcatgagccc gaagtggcga gcccgatctt   5160
ccccatcggt gatgtcggcg atataggcgc cagcaaccgc acctgtggcg ccggtgatgc   5220
```

```
cggccacgat gcgtccggcg tagaggatcg agatctcgat cccgcgaaat taatacgact    5280
cactata                                                              5287
```